United States Patent [19]

Melchior, Jr. et al.

[11] Patent Number: 4,824,668
[45] Date of Patent: Apr. 25, 1989

[54] ATTENUATED INFECTIOUS BURSAL DISEASE VIRUS STRAIN AND VACCINE THEREFROM

[75] Inventors: Fred W. Melchior, Jr., Frankford; Lillian Melson, Millsboro, both of Del.

[73] Assignee: Sterwin Laboratories Inc., Millsboro, Del.

[21] Appl. No.: 23,612

[22] Filed: Mar. 9, 1987

[51] Int. Cl.$^4$ .................. A61K 35/76; A61K 39/12
[52] U.S. Cl. ..................................... 424/89; 435/235
[58] Field of Search ........................ 424/89; 435/235

[56] References Cited

U.S. PATENT DOCUMENTS

| | | | |
|---|---|---|---|
| 3,548,055 | 12/1970 | Moulthrop | 424/89 |
| 3,769,400 | 10/1973 | Bengelsdorff | 424/89 |
| 4,481,188 | 11/1984 | Apontowell et al. | 424/89 |
| 4,530,831 | 7/1985 | Lutticken et al. | 424/89 |

Primary Examiner—Howard E. Schain
Attorney, Agent, or Firm—Wendell R. Guffey; Thomas L. Farquer

[57] ABSTRACT

A novel strain of attenuated infectious bursal disease virus VR2161, an infectious bursal disease vaccine containing the attenuated infectious bursal disease virus strain, and a method for controlling infectious bursal disease in po

ATTENUATED INFECTIOUS BURSAL DISEASE VIRUS STRAIN AND VACCINE THEREFROM

The present invention relates generally to poultry viruses and vaccines therefrom and particularly to a novel strain of attenuated infectious bursal disease virus, an infectious bursal disease vaccine containing the attenuated infectious bursal disease strain, and a method for controlling infectious bursal disease in poultry.

BACKGROUND OF THE INVENTION

Infectious Bursal Disease (IBD), also known as Gumboro Disease, in poultry is caused by the Infectious Bursal Disease Virus (IBVD). The disease infects poultry worldwide and is responsible for large economic losses in the poultry industry. The disease causes diarrhea, muscular hemorrhages, inflammations, bleeding, damage to the immune system, and necrosis of the Bursa of fabricii and rectum. In infected poultry, the mortality is high and the surviving animals show retarded growth and insufficient feed utilization. Young animals 1-6 weeks old are particularly susceptible to the disease.

Several vaccines have been produced to control IBD. The IBDV has been isolated from the Bursa of fabricii and other organs in infected animals and used to produce live or inactivated viruses propagated in chicken embryos, newborn mice, or cultures containing bursa cells or chicken embryo cells. U.S. Pat. No. 3,548,055 discloses an IBD vaccine prepared from IBDV in which the virus was attenuated by passing the virus through at least eight consecutive passages in embryonic eggs. U.S. Pat. No. 3,769,400 discloses an IBD vaccine prepared from IBDV in which the virus was passed 18-25 times through immuno-suppressed baby mice. U.S. Pat. No. 4,530,831 discloses an IBD vaccine prepared by propagating an IBDV on chicken embryo fibroblast (CEF) cultures prepared from specific pathogen free (SPF) eggs. These vaccines, although not fatal, still produce some IBD symptoms in the vaccinated poultry, particularly gross and histological lesions on the Bursa of fabricii.

These prior art vaccines also share another common problem: the vaccines that can be administered to the animals by mass administration techniques remain sufficiently virulent to produce symptoms of the disease in the vaccinated animal, particularly necrosis or atrophy of the Bursa of fabricii; and the vaccines that have been attenuated to eliminate the symptoms of the disease when administered cannot be administered using mass administration techniques, these vaccines must be injected into each individual animal. Administering the vaccines through mass administration methods such as in drinking water or by spraying is simple, efficient, and not labor intensive. Injecting each animal is costly, time consuming, and labor intensive.

There exists, therefore, a continuing need for new and improved vaccines to combat IBD. There is a particular need for a vaccine containing an attenuated IBDV strain which can be administered using mass administration methods but which does not produce IBD symptoms in the vaccinated animal, particularly necrosis of the Bursa of fabricii.

SUMMARY OF THE INVENTION

It is, therefore, an object of the present invention to provide a novel strain of attenuated infectious bursal disease virus (IBDV).

It is another object of the present invention to provide a vaccine containing an attenuated IBDV for use with poultry.

It is another object of the present invention to provide a vaccine containing inactivated IBDV for use with poultry.

It is another object of the present invention to provide a method for controlling IBD in poultry.

It is a further object of the present invention to provide a vaccine containing a novel strain of IBDV that does not produce gross or histological lesions on the Bursa of fabricii when administered using mass administration methods.

These and other objects are achieved by passing a virulent IBDV strain in embryonated eggs and chicken embryo fibroblasts (CEF) for a sufficient number of passages to produce an attenuated IBDV strain. The attenuated IBDV strain is used, live or inactivated, to prepare a vaccine which can be administered to poultry to control IBD. The vaccines of the present invention may also contain an inert pharmaceutically acceptable carrier or diluent, one or more adjuvants, one or more stabilizers, and one or more other avian viruses.

The vaccine according to the present invention is administered in amounts sufficient to stimulate the immune system and confer resistance to IBD. The vaccine can be administered using mass administration methods but does not produce IBD symptoms, particularly necrosis or atrophy of the Bursa of fabricii, in the vaccinated animal.

Other objects, advantages, and novel features of the present invention will become apparent from the following detailed description of the invention.

DETAILED DESCRIPTION OF THE INVENTION

The attenuated infectious bursal disease virus (IBDV) strain of the present invention was prepared from a virulent IBDV strain received from the University of Delaware, identified as IBD isolate, 1084 Variant E, 20% w/v bursal homogenate #061285 in a multi-step attenuation process.

First, a virus seed stock was prepared by infecting embryonated eggs, harvesting the embryos following death, and using these embryos to prepare an homogenate. This homogenate was prepared in IBD stabilizer as a 25% w/v suspension. Aliquots were dispensed in vials and stored at $-90°$ F. This suspension was identified as embryo passage I, E-1 #121685.

The Master Seed Virus for this vaccine was produced by adapting and passaging the E-1, #121685 virus in chicken embryo fibroblast cells. During this passaging sequence, a plaque purification procedure was used on three separate passages. Plaque purification was accomplished by using an agar overlay followed by selection and harvest of an individual plaque. Virus from this plaque was used to infect additional cell cultures. A total of 22 tissue culture passages were completed on this virus.

Following the last cell culture passage, virus was harvested and used to infect embryonated eggs. Infected embryos were harvested 4 days post-inoculation and a 25% w/v homogenate prepared in IBD stabilizer. This virus was designated as Master Seed virus and labeled $E_1$, $TC_{22}$, $E_1$, #061686.

Subsequent passages were conducted in a similar manner to produce Working Seed ($E_1$ $TC_{22}$ $E_2$) and Production Seed virus ($E_1$ $TC_{22}$ $E_3$). Production Seed was used to inoculate eggs and prepare a Vaccine Virus ($E_1 TC_{22} E_4$) for vaccine production.

$E_1 TC_{22} E_4$ Vaccine Virus, Serial #2703, has been deposited with the American Type Culture Collection, Rockville, Md. and been assigned the accession number VR2161. Applicants have directed that the deposited IBDV strain be freely available to the general public upon issuance of a U.S. Patent citing the strain.

The novel attenuated IBDV strain of the present invention has the following distinguishing characteristics which make it useful in a vaccine: (1) the attenuated IBDV strain is fully adapted to growth and reproduction in cell cultures, particularly chicken embryo fibroblasts (CEF), (2) the attenuated IBDV strain does not produce IBDV symptoms when administered to poultry, and (3) the attenuated IBDV strain does not produce gross or histological lesions in the Bursa of fabricii of poultry when administered by mass administration methods such as administering the vaccine in drinking water, by spraying the animal's environment, or by injection at about one day of age.

According to the present invention, a vaccine for the control of IBD in poultry comprises an attenuated IBDV strain, VR2161, and an inert pharmaceutically acceptable carrier or diluent. Preferably the carrier or diluent is one compatible with vaccine administration by mass administration techniques. However, the carrier or diluent may also be compatible with other administration methods such as injection, eye drops, nose drops, and the like.

The attenuated vaccine according to the present invention is administered in amounts sufficient to stimulate the immune system and confer resistance to IBD. Preferably the vaccine is administered in dosages ranging from abou log 2 to about log 5 $EID_{50}$ (EID=Embryo Infective Dose), preferably between about log 3 to about log 4 $EID_{50}$.

According to the present invention, a vaccine for the control of IBD in poultry comprises an inactivated virus prepared from an attenuated IBDV strain, VR2161. The attenuated virus is harvested from embryos or CEF's and inactivated using any known technique such as inactivation with formaldehyde, phenol, UV or gamma radiation, beta-propiolactone, and the like. The inactivated virus is separated from the inactivating agent and used to prepare a vaccine.

The vaccine containing the inactivated IBDV according to the present invention is administered in amounts sufficient to stimulate the immune system and confer resistance to IBD. Preferably the vaccine is administered in dosages ranging from about log 5 to about log 8 $EID_{50}$, preferably between about log 6 to about log 7 $EID_{50}$.

Vaccines according to the present invention, preferably the vaccine containing the inactivated IBDV, may contain combinations of the attenuated or inactivated IBDV of the present invention and one or more unrelated avian viruses, preferably New Castle Disease Virus, Infectious Bronchitis Virus, Reo Virus, Adeno Virus, and other IBDV strains. For combination vaccines, inactivated antigens can be added to the IBDV of the present invention in a dosage which fulfills the requirements for inactivated vaccines according to 9 C.F.R. 113-120, in particular, for combined vaccines containing New Castle Disease Virus (NDV), the requirements of 9 C.F.R. 113-125.

The vaccines of the present invention may also contain one or more adjuvants. Any suitable adjuvant can be used including chemical and polypeptide immunostimulants which enhance the immune systems' response to antigens. Preferably, adjuvants such as aluminum hydroxide, aluminum phosphate, plant and animal oils, and the like are administered with the vaccine in amounts sufficient to enhance the immune response to the IBDV. The amount of adjuvant added to the vaccine will vary depending on the nature of the adjuvant, generally ranging from about 0.1 to about 100 times the weight of the IBDV, preferably from about 1 to about 10 times the weight of the IBDV.

The vaccines of the present invention may also contain various stabilizers. Any suitable stabilizer can be used including carbohydrates such as sorbitol, manitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

Techniques for preparing the vaccines of the present invention are well known to those skilled in the art. Generally this vaccine is produced by inoculation of 10 day embryos with seed virus via the chorio-allantoic sac route and harvesting the infected embryos approximately 4 days post inoculation. These embryos are homogenized and processed to obtain the virus which is batched with other components to produce a serial of vaccine.

According to the present invention, a method is provided for controlling IBD in poultry comprising administering to the poultry a vaccine prepared from an attenuated IBDV strain, VR2161.

The attenuated vaccine can be administered by any suitable method including nasally, ophthalmically, by injection, in drinking water, in feed, by exposure, and the like. Preferably, the vaccine is administered by mass administration techniques such as administering the vaccine in drinking water or by spraying the animals environment. A vaccine containing live or inactivated IBDV according to the present invention can be administered by injection. When administered by injection, the vaccines are preferably administered parenterally. Parenteral administration as used herein means administration by intravenous, subcutaneous, intramuscular, or intraperitoneal injection. Known techniques such as Beak-o-Vac administration are preferred.

The vaccines of the present invention are administered to the poultry any time after hatching. Preferably, the vaccines are administered between the time of birth and about 20 weeks of age.

The vaccines of the present invention are administered to poultry to prevent IBD. Poultry includes chickens, roosters, hens, broilers, roasters, turkeys, and ducks.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

SAFETY OF IBD-187 EV MASTER SEED VIRUS E1 TC22 E1 #061686

The passage level of IBD-187 EV Master Seed Virus E1 TC22 E1 #061686 was tested for safety in two separate trials.

In Trial 1, groups of susceptible one day old chickens were injected subcutaneously with either a 1x dose or a 10x dose of IBD-187 EV Master Seed Virus.

In Trial 2 three week old susceptible chickens were injected subcutaneously with a 1x dose of Master Seed Virus.

Each trial had negative and positive controls.

The results of both trials indicated that IBD-187 EV Master Seed Virus did not induce bursal lesions or atrophy when injected in one day and three week old chickens.

Trial 1

Trial 1 consisted of four groups of one day old susceptible SCWL chickens. For group 1, twenty-five chickens were injected subcutaneously with a 1x dose of IBD-187 EV Master Seed Virus ($E_1$ $TC_{22}$ $E_1$ #061686). For vaccination, one vial of Master Seed Virus was rehydrated in 200 ml of sterile Marek's diluent. Each chick received 0.2 ml of the rehydrated virus by subcutaneous injection (approximately $10^{4.20} EID_{50}$/bird). For group 2, twenty-five chickens were injected subcutaneously with a 10x dose of IBD-187 EV Master Seed Virus. For vaccination, one vial of Master Seed Virus was rehydrated in 20 ml of sterile Marek's diluent. Each chicken received 0.2 ml by subcutaneous injection (approximately $10^{5.20} EID_{50}$/bird). For group 3, ten chickens were held as unvaccinated negative controls. For group 4, ten chickens (unvaccinated) were challenged at thirteen days of age with IBD-Variant E Challenge Virus E-1 #121685 to serve as positive controls.

Twenty-one days post-vaccination, all vaccinates, positive controls, and negative controls were killed and individually weighed. Bursae were harvested from each chicken and weighed. Bursa/body weight ratios were then calculated and a standard deviation computed. All chickens were held in the Horsfal isolation cages for the duration of the trial. The necropsy results are shown in Tables 1, 2, and 3.

Referring to Tables 1, 2, and 3, at the end of the three week period, no incidence of bursal lesions or atrophy was found in either the 1x vaccinates, 10x vaccinates, or negative controls. Severe bursal atrophy was present in all positive control chickens following an eight day challenge period. Average body/bursa weight ratios calculated for each group showed that both vaccinated groups fell within the normal range (2.88 grams (gms) to 6.92 gms as determined by calculations of a standard deviation of the negative control group) with an average ratio of 5.3 for the 1x group and 5.8 for the 10x group. The positive controls had an average ratio of 1.47, indicating severe bursal atrophy.

Trial 2

Trial 2 consisted of three groups of susceptible Spafas SCWL chickens, three weeks of age. For group 1, thirty-five chickens were vaccinated with one dose of IBD-187 EV Master Seed Virus. For vaccination, one vial of Master Seed Virus was rehydrated in 200 ml of sterile Marek's diluent. Each chicken was injected, subcutaneously with 0.2 ml of virus (approximately $10^{4.20}$ $EID_{50}$). For group 2, each of twenty chickens was challenged with IBD-Variant E CV E-1 #121685. For group 3, twenty chickens were held as unvaccinated negative controls.

Four days post-vaccination, 10 chickens from each group were necropsied and examined for gross IBD bursal lesions. Fourteen days post-vaccination, the remaining vaccinates, positive controls, and negative controls were killed and individually weighed. An eight day challenge period was used for the positive controls, rather than the standard four day period. Bursae were harvested from each chicken and weighed. Bursal/body weight ratios were then calculated and a standard deviation computed. All chickens were held in the Horsfal isolation cages for the duration of the trial. The necropsy results are shown in Tables 1, 2, and 4.

Referring to Tables 1, 2, and 4, the four day necropsy results indicated no incidence of bursal lesions in either the vaccinates or the negative controls while 100 percent of the positive controls succumbed to challenge.

The remaining vaccinates and negative controls exhibited no gross bursal lesions or atrophy after the two week period. The average bursa/body weight ratios were 4.1 for the vaccinates, 4.2 for the negative controls, and 0.9 for the positive controls. The normal range as determined by calculation of a standard deviation of the negative control group was 1.32 to 7.8.

For purposes of this safety test, bursal atrophy was measured by comparing the bursa/body weight ratios of the vaccinates and positive controls to the negative controls. All chickens were individually weighed to the nearest 0.1 g. Bursae were then harvested and weighed to the nearest 0.01 g and bursa/body weight ratios computed for each bird by using the formula: Bursa weight/Body weight x 1000.

An average ratio was calculated for each group. A standard deviation was then calculated for the control group using the formula: $S = [(X - A)^2/(N - 1)]^{0.5}$; whereby X represents the ratio of each individual bird in the control group, A the average ratio for the controls, and N the total number of birds in the group. Infected groups must show more than two standard deviations difference to be considered significant. The same procedure, hereinafter referred to as "statistical method", is used in several examples herein.

TABLE 1

| Treatment | No. of Birds | Age | Necropsy Results No. of Birds Positive/Total | Percent Affected |
|---|---|---|---|---|
| TRIAL 1 21 DAY NECROPSY RESULTS | | | | |
| 1 × dose IBD-EV Master Seed Virus E1 TC22 E1 #061686 | 25 | 1 Day | 0/25 | 0 |
| 10 × dose IBD-EV Master Seed Virus E1 TC22 E1 #061686 | 25 | 1 Day | 0/25 | 0 |
| Negative Controls | 10 | 1 Day | 0/10 | 0 |
| Positive Controls | 10 | 1 Day | 10/10* | 100 |
| TRIAL 2 4 DAY NECROPSY RESULTS | | | | |
| 1 × dose IBD-EV Master Seed Virus E1 TC22 E1 #061686 | 10 | 3 Weeks | 0/10 | 0 |
| Negative Controls | 10 | 3 Weeks | 0/10 | 0 |

TABLE 1-continued

| Treatment | No. of Birds | Age | Necropsy Results No. of Birds Positive/Total | Percent Affected |
|---|---|---|---|---|
| Positive Controls | 10 | 3 Weeks | 10/10 | 100 |

*Lesions were based on severe bursal atrophy 8 days post-challenge.

TABLE 2
SUMMARY OF BODY AND BURSA WEIGHTS

TRIAL 1

| Group | Average Ratio | Standard Deviation |
|---|---|---|
| Negative Controls | 4.9 | 1.01* |
| Positive Controls | 1.47 | |
| Vaccinates - 1 × | 5.3 | |
| Vaccinates - 10 × | 5.8 | |

*Range for calculating significance of ratios is two standard deviations or 2.02. Therefore, for purposes of this test, normal range is 2.88 to 6.92.

TRIAL 2

| Group | Average Ratio | Standard Deviation |
|---|---|---|
| Negative Controls | 4.2 | 1.44* |
| Positive Controls | 0.9 | |
| Vaccinates | 4.1 | |

*Range for calculating significance of ratios is two standard deviations or 2.88. Therefore, for purpose of this test, normal range is 1.32 to 7.08.

TABLE 3
TRIAL 1 - BODY AND BURSA WEIGHTS

| Bird ID Number | Body Weight (Gms) | Bursa Weight (Gms) | Bursa/Body Weight Ratio |
|---|---|---|---|
| VACCINATES - 1 × DOSE | | | |
| 211 | 209.1 | 1.54 | 7.4 |
| 212 | ND | ND | ND |
| 213 | 188.0 | 0.64 | 3.4 |
| 214 | 163.5 | 0.87 | 5.3 |
| 215 | 155.7 | 0.72 | 4.6 |
| 216 | 174.9 | 1.66 | 9.5 |
| 217 | 188.2 | 0.89 | 4.7 |
| 218 | 212.7 | 1.11 | 5.2 |
| 219 | 206.0 | 1.16 | 5.6 |
| 220 | 195.0 | 0.84 | 4.3 |
| 221 | 207.8 | 0.63 | 3.0 |
| 222 | 152.0 | 0.53 | 3.5 |
| 223 | 202.0 | 0.89 | 4.4 |
| 224 | 194.0 | 0.82 | 4.2 |
| 225 | 187.8 | 1.18 | 6.3 |
| 226 | 186.0 | 1.24 | 6.7 |
| 227 | 234.0 | 1.16 | 5.0 |
| 228 | 175.7 | 0.93 | 5.3 |
| 229 | 252.7 | 1.56 | 6.2 |
| 230 | 151.4 | 0.52 | 3.4 |
| 231 | 219.5 | 1.32 | 6.0 |
| 232 | 241.9 | 1.15 | 4.8 |
| 233 | 186.3 | 1.13 | 6.1 |
| 234 | 188.6 | 1.22 | 6.5 |
| 235 | 192.1 | 1.08 | 5.6 |
| Average Ratio: 5.3 | | | |
| VACCINATES - 10 × DOSE | | | |
| 236 | 210.3 | 1.00 | 4.8 |
| 237 | 201.2 | 1.43 | 7.1 |
| 238 | 195.1 | 1.11 | 5.7 |
| 239 | 198.5 | 1.29 | 6.5 |
| 240 | 186.7 | 1.02 | 5.5 |
| 241 | 193.8 | 0.93 | 4.8 |
| 242 | ND | ND | ND |
| 243 | 196.1 | 1.43 | 7.3 |
| 244 | 222.3 | 1.26 | 5.7 |
| 245 | 221.9 | 1.66 | 7.5 |
| 246 | 247.8 | 1.64 | 6.6 |
| 247 | ND | ND | ND |
| 248 | 159.5 | 0.74 | 4.6 |
| 249 | 211.0 | 1.15 | 5.5 |
| 250 | 221.8 | 1.14 | 5.1 |
| 251 | 199.4 | 1.36 | 6.8 |
| 252 | 200.0 | 1.24 | 6.2 |
| 253 | 187.7 | 0.85 | 4.5 |
| 254 | 180.3 | 1.06 | 5.9 |
| 255 | 226.1 | 1.66 | 7.3 |
| 256 | 200.7 | 1.18 | 5.9 |
| 257 | 229.1 | 1.41 | 6.2 |
| 258 | 208.0 | 0.79 | 3.8 |
| 259 | 200.0 | 1.14 | 5.7 |
| 260 | 212.2 | 1.04 | 4.9 |
| Average Ratio: 5.8 | | | |
| NEGATIVE CONTROLS | | | |
| 1 | 186.2 | 1.0 | 5.4 |
| 2 | 155.3 | 0.49 | 3.2 |
| 3 | 185.8 | 1.18 | 6.4 |
| 4 | 206.6 | 1.0 | 4.8 |
| 5 | 216.8 | 1.11 | 5.1 |
| 6 | 199.1 | 0.81 | 4.1 |
| 7 | 194.4 | 0.82 | 4.2 |
| 8 | 174.5 | 1.04 | 6.0 |
| 9 | 191.4 | 0.81 | 4.2 |
| 10 | 172.3 | 1.02 | 5.9 |
| Average Ratio: 4.9 | | | |
| POSITIVE CONTROLS | | | |
| 401 | 160.5 | 0.21 | 1.3 |
| 402 | 146.4 | 0.26 | 1.8 |
| 403 | 167.5 | 0.26 | 1.6 |
| 404 | 162.3 | 0.26 | 1.6 |
| 405 | 165.7 | 0.24 | 1.4 |
| 406 | 182.6 | 0.23 | 1.3 |
| 407 | 157.5 | 0.27 | 1.7 |
| 408 | 179.1 | 0.24 | 1.3 |
| 409 | 176.0 | 0.24 | 1.4 |
| 410 | 200.3 | 0.26 | 1.3 |
| Average Ratio: 1.47 | | | |

TABLE 4
TRIAL 2 - BODY AND BURSA WEIGHTS

| Bird ID Number | Body Weight (Gms) | Bursa Weight (Gms) | Bursa/Body Weight Ratio |
|---|---|---|---|
| VACCINATES | | | |
| 281 | 259.3 | 1.22 | 4.7 |
| 282 | 379.7 | 1.43 | 3.7 |
| 283 | 349.0 | 1.29 | 3.7 |
| 284 | 239.1 | 1.11 | 4.6 |
| 285 | 315.1 | 1.33 | 4.2 |
| 286 | 269.9 | 1.18 | 4.4 |
| 287 | 340.5 | 1.58 | 4.6 |
| 288 | 251.4 | 0.86 | 3.4 |
| 289 | 285.5 | 1.14 | 4.0 |
| 290 | 242.4 | 1.17 | 4.8 |
| 291 | 294.3 | 1.57 | 5.3 |
| 292 | 319.4 | 1.29 | 4.0 |
| 293 | 318.9 | 1.33 | 4.2 |
| 294 | 266.2 | 1.06 | 4.0 |
| 295 | 346.8 | 1.28 | 3.7 |
| 296 | 334.5 | 1.38 | 4.1 |
| 297 | 306.5 | 1.16 | 3.8 |
| 298 | 328.0 | 1.22 | 3.7 |
| 299 | 288.7 | 1.21 | 4.2 |
| 300 | 378.0 | 1.56 | 4.1 |
| 301 | 292.7 | 1.07 | 3.7 |
| 302 | 336.1 | 1.43 | 4.3 |
| 303 | 299.8 | 0.92 | 3.1 |
| 304 | 307.1 | 1.24 | 4.0 |
| 305 | 287.1 | 0.91 | 3.2 |
| Average Ratio: 4.1 | | | |
| NEGATIVE CONTROLS | | | |
| 1 | 310.0 | 1.27 | 4.1 |
| 2 | 365.1 | 1.39 | 3.8 |
| 3 | 351.1 | 2.78 | 7.9 |
| 4 | 403.5 | 1.63 | 4.0 |
| 5 | 354.2 | 1.12 | 3.2 |
| 6 | 364.8 | 1.66 | 4.6 |
| 7 | 359.1 | 1.11 | 3.1 |
| 8 | 314.3 | 0.86 | 2.7 |
| 9 | 266.3 | 1.24 | 4.7 |
| 10 | 314.8 | 1.35 | 4.3 |

TABLE 4-continued

TRIAL 2 - BODY AND BURSA WEIGHTS

| Bird ID Number | Body Weight (Gms) | Bursa Weight (Gms) | Bursa/Body Weight Ratio |
|---|---|---|---|
| Average Ratio: 4.20 | | | |
| POSITIVE CONTROLS | | | |
| 326 | 226.1 | 0.18 | 0.8 |
| 327 | 240.2 | 0.25 | 1.0 |
| 328 | 226.4 | 0.23 | 1.0 |
| 329 | 208.9 | 0.18 | 0.86 |
| 330 | 224.0 | 0.18 | 0.8 |
| 331 | 221.1 | 0.18 | 0.81 |
| 332 | 247.5 | 0.17 | 0.69 |
| 333 | 255.7 | 0.29 | 1.1 |
| 334 | 290.1 | 0.30 | 1.0 |
| 335 | 311.5 | 0.27 | 0.87 |
| Average Ratio: 0.9 | | | |

EXAMPLE II

SAFETY OF IBD-187EV MASTER SEED VIRUS E1 TC22 E1 #061686

The passage level of IBD-187 EV Master Seed Virus E1 TC22 E1 #061686 was tested for safety. For this trial, three week old susceptible SCWL chickens were injected subcutaneously with a minimum protective dose of IBD-187EV experimental vaccine, E-4 #081886. Negative and positive controls were included.

This trial consisted of three groups of susceptible SCWL chickens, three weeks of age. For Group 1, 35 chickens were vaccinated with approximately one minimum protective dose of vaccine virus. For vaccination, two vials of experimental IBD-187EV vaccine (E4 #081886) were rehydrated in a total of 400 milliliters (ml) of sterile Marek's diluent. A further dilution of 1:5 was prepared. Each chicken was then injected subcutaneously with 0.2 ml of the final vaccine dilution (approx. $10^{2.63} EID_{50}$/bird). For Group 2, each of 20 chickens was challenged with IBD Variant E CV E-1 #121685, and isolated as positive controls. For Group 3, 20 chickens were held as unvaccinated negative controls. All chickens were held in Horsfal isolation cages for the duration of the trial.

Four days post-vaccination, 10 chickens from each group were necropsied for gross IBD bursal lesions. Fourteen days post-vaccination, the remaining vaccinates, positive controls, and negative controls were killed, individually weighed, and necropsied for gross bursal lesions. Bursae were harvested from each chicken and weighed. Bursal/body weight ratios were then calculated and a standard deviation computed. The results were calculated using the statistical methods in Example I. The necropsy results are shown in Tables 5, 6, and 7.

Referring to Tables 5, 6, and 7, the four day necropsy results indicated no incidence of bursal lesions in either the vaccinates or the negative controls while 100% of the positive controls succumbed to challenged. The remaining vaccinates and negative controls exhibited no gross bursal lesions or atrophy after the two week period. The average bursa/body weight ratios were 5.1 for the vaccinates, 4.7 for the negative controls, and 0.80 for the positive controls. The normal range as determined by calculation of a standard deviation of the negative control group was 1.82 to 7.58.

TABLE 5

NECROPSY RESULTS

| TREATMENT | # BIRDS | # BIRDS POSITIVE/ TOTAL | % AFFECTED |
|---|---|---|---|
| 4 DAY NECROPSY RESULTS | | | |
| IBD-187EV Vaccine E4 #081886 (1:5 dil) | 10 | 0/10 | 0 |
| Negative Controls | 10 | 0/10 | 0 |
| Positive Controls | 10 | 10/10 | 100 |
| 14 DAY NECROPSY RESULTS | | | |
| IBD-187EV Vaccine E4 #081886 (1:5 dil) | 25 | 0/25 | 0 |
| Negative Controls | 10 | 0/10 | 0 |
| Positive Controls | 10 | 10/10* | 100 |

*Lesions were based on severe bursal atrophy

TABLE 2

SUMMARY OF BODY AND BURSA WEIGHTS

| GROUP | AVERAGE RATIO | STANDARD DEVIATION |
|---|---|---|
| Vaccinates | 5.1 | — |
| Negative Controls | 4.7 | 1.44* |
| Positive Controls | 0.80 | — |

*Range for calculating significance of ratios is two standard deviations or 2.88. Therefore, for purposes of this test, normal range is 1.82 to 7.58.

TABLE 7

BODY AND BURSA WEIGHTS

| BIRD ID | BODY WGT (GMS) | BURSA WGT (GMS) | BURSA/BODY WGT RATIO |
|---|---|---|---|
| NEGATIVE CONTROLS | | | |
| 11 | 248.2 | 1.09 | 4.4 |
| 12 | 248.2 | 1.59 | 6.4 |
| 13 | 338.8 | 1.26 | 3.7 |
| 14 | 260.4 | 1.07 | 4.1 |
| 15 | 244.4 | 0.95 | 3.9 |
| 16 | 275.6 | 1.77 | 6.4 |
| 17 | 313.7 | 2.09 | 6.7 |
| 18 | 260.5 | 1.58 | 6.1 |
| 19 | 247.1 | 0.69 | 2.8 |
| 20 | 252.4 | 0.71 | 2.8 |
| Avg. Ratio: 4.7 | | | |
| Std. Deviation: 1.44 | | | |
| POSITIVE CONTROLS | | | |
| 856 | 260.5 | 0.20 | 0.8 |
| 857 | 251.9 | 0.20 | 0.8 |
| 858 | 265.8 | 0.25 | 0.9 |
| 859 | 238.3 | 0.28 | 0.8 |
| 860 | 416.7 | 0.32 | 0.8 |
| 861 | 267.2 | 0.22 | 1.0 |
| 862 | 251.7 | 0.24 | 0.9 |
| 863 | 301.9 | 0.27 | 0.8 |
| 864 | 216.5 | 0.18 | 0.8 |
| 865 | 273.0 | 0.21 | 0.8 |
| Avg. ratio: 0.80 | | | |
| NEGATIVE CONTROLS-VACCINATES | | | |
| 821 | 284.7 | 1.37 | 4.8 |
| 822 | 229.0 | 0.84 | 3.7 |
| 823 | 267.4 | 1.93 | 7.2 |
| 824 | 207.5 | 0.94 | 4.5 |
| 825 | 196.5 | 1.03 | 5.2 |
| 826 | 332.7 | 1.92 | 5.8 |
| 827 | 270.2 | 1.10 | 4.1 |
| 828 | 357.3 | 1.76 | 4.9 |
| 829 | 286.2 | 1.20 | 4.3 |
| 830 | 205.5 | 0.54 | 2.6 |
| 831 | 243.1 | 1.57 | 6.5 |
| 832 | 290.0 | 1.12 | 3.9 |
| 833 | 232.7 | 1.06 | 4.6 |
| POSITIVE CONTROLS-VACCINATES | | | |
| 834 | 238.3 | 1.00 | 4.2 |
| 835 | 290.9 | 2.35 | 8.1 |
| 836 | 267.8 | 1.00 | 3.7 |
| 837 | 292.8 | 2.39 | 8.2 |
| 838 | 314.1 | 1.56 | 5.0 |

TABLE 7-continued

BODY AND BURSA WEIGHTS

| BIRD ID | BODY WGT (GMS) | BURSA WGT (GMS) | BURSA/BODY WGT RATIO |
|---|---|---|---|
| 839 | 254.0 | 1.71 | 6.7 |
| 840 | 359.0 | 1.79 | 5.0 |
| 841 | 241.1 | 1.11 | 4.6 |
| 842 | 293.9 | 1.52 | 5.2 |
| 843 | 223.6 | 0.91 | 4.1 |
| 844 | 272.0 | 1.32 | 4.9 |
| 845 | 223.9 | 1.26 | 5.6 |

Avg. ratio: 5.1

EXAMPLE III

ANTIGENICITY OF IBD-187EV MASTER SEED VIRUS ($E_1 TC_{22} E1$) SUBCUTANEOUS ROUTE OF APPLICATION AT ONE DAY OF AGE

The highest level of IBD-187EV Master Seed Virus ($E_1 TC_{22} E_1$ #061686) represented in final commercial vaccine was tested for antigenicity. The tests were conducted using susceptible chickens, one day of age. IBD-187EV dried vaccine ($E_4$ #081886) was diluted and administered by subcutaneous route at one day of age.

Vaccine Titration

Three vials of IBD-187EV experimental vaccine ($E_4$ #081886) were rehydrated in a total of 600 ml of IBD stabilizer. A 1:20 dilution was prepared by mixing 2 ml of the pooled vaccine with 38 ml of stabilizer. A set of five replicate tetrations was done on this final vaccine dilution at the time of bird vaccination using 10 day old embryonated eggs. Based on five replicate titrations, IBD187EV Vaccine ($E_4$ #081886; 1:20 dilution) had a titer of $10^{3.02} EID_{50}$/ml. Since each ml vaccinates five chickens, this corresponds to a dose titer of $10^{2.32} EID_{50}$/bird. IBD-187EV vaccine ($E_4$ #081886) passed the test requirements listed in 9CFR 113.166. Vaccine serials produced from IBD-187EV Master Seed Virus ($E_1 TC_{22}$ #061686) are required to have a titer of $10^{3.02} EID_{50}$/dose through expiration and $10^{3.32} EID_{50}$/dose at release.

Vaccination

For this trial, three groups of one day old susceptible chickens were used. Group 1 consisted of 35 chickens vaccinated via subcutaneous injection with IBD-187 EV experimental vaccine ($E_4$ #081886; 1:20 dilution). Group 2 consisted of 12 chickens held as unvaccinated controls for IBD challenge. Group 3 consisted of 12 unvaccinated chickens to be held as unchallenged negative controls. Extra chicks were immunized to allow for normal chick mortality during the first two weeks of life. Chickens were held in Horsfal isolation cages until challenged.

Challenge

Three weeks post-vaccination, 32 vaccinates and 10 controls were challenged with IBD Variant E Challenge Virus, $E_1$ #121685. Ten controls were held as unchallenged negative controls.

Nine days post-challenge, all chickens were killed, individually weighed, and necropsied for gross IBD bursal lesions. Bursae were then harvested from each chicken and weighed. The results were calculated using the statistical methods in Example I. The nine day necropsy results are shown in Tables 8 and 9.

Referring to Tables 8 and 9, no incidence of bursal lesions were found in either the vaccinated chickens or the negative controls while 100% of the positive controls exhibited lesions, including severe bursal atrophy. The standard deviation computed from the negative control group was 1.6. Since the average ratio of the control group was 5.9, the normal range for this trial was 2.7 to 9.1 as normal range equals two standard deviations. The average ratio for the vaccinates (4.9) fell within this range while the average ratio for the positive controls (1.1) did not meet normal range.

TABLE 8

NINE DAY NECROPSY RESULTS

| GROUP | TREATMENT | ROUTE | VACCINE DOSE/BIRD | # BIRDS | POST-CHAL. LESIONS # POS/TOTAL | % PROT. |
|---|---|---|---|---|---|---|
| 1 | IBD-187EV Vac. $E_4$ #081886 (1:20 dilution) | S.C. | $10^{2.32}$ | 32 | 0/32 | 100 |
| 2 | Negative Controls (Unchallenged) | — | — | 10 | 0/10 | —* |
| 3 | Positive Controls | — | — | 10 | 10/10 | 0** |

*Protection was not measured as birds were unchallenged.
**Lesions included severe bursal atrophy.

TABLE 9

SUMMARY OF BURSA/BODY WEIGHT RATIOS

| TREATMENT GROUP | AVG. BURSA/BODY WEIGHT RATIO | STANDARD DEVIATION* |
|---|---|---|
| Vaccinates | 4.9 | — |
| Positive Controls | 1.1 | — |
| Negative Controls | 5.9 | 1.6 |

*Range for determining significancy of average ratios is two standard deviations or 3.2. Therefore, for purposes of this test, normal range is 2.7 to 9.1.

EXAMPLE IV

ANTIGENICITY OF IBD-187EV MASTER SEED VIRUS E1 TC22 E1 #061686 DRINKING WATER ROUTE OF APPLICATION

The highest level of IBD-187EV Master Seed Virus E1 TC22 E1 #061686 represented in final commercial vaccine was tested for antigenicity. The tests were conducted using susceptible SCWL chickens, two weeks of age. IBD-187EV dried vaccine ($E_4$ #081886) was diluted 1:10 and administered via the drinking water at two weeks of age.

Vaccine titration

Three vials of IBD-187EV experimental vaccine ($E_4$ #081886) were rehydrated in a total of 90 ml of IBD stabilizer. A 1:10 dilution was prepared by mixing two ml of the pooled vaccine with 18 ml of stabilizer. A set of five replicate titrations was done on this final vaccine dilution at the time of bird vaccination using 10 day old embryonated eggs. Based on five replicate titrations, IBD-187EV vaccine ($E_4$ #081886; 1:10 dilution) had a titer of $10^{4.09}EID_{50}$/ml. This corresponds to a dose of $10^{2.59}EID_{50}$/bird. IBD-187EV vaccine ($E_4$ #081886) passed the test requirements listed in 9CFR 113.166. Vaccine serials produced from IBD-187EV Master Seed Virus E1 TC22 E1 #061686 are required to have a titer of $10^{3.29}EID_{50}$ through expiration and $10^{3.59}EID_{50}$ at release.

Vaccination

For this trial, 35 susceptible SCWL, two weeks of age, were vaccinated with IBD-187EV experimental vaccine ($E_4$ #081886; 1:10 dilution) via the drinking water. Following vaccination, the chickens were held in a colony test house. Twenty-five unvaccinated chickens were held for negative and positive controls.

Challenge

Twenty-two days post-vaccination, 30 vaccinates and 10 controls were challenged with IBD variant E challenge virus, $E_1$ #121685. Ten controls were held as unchallenged negative controls.

Nine days post-challenge, all chickens were killed, individually weighed, and necropsied for gross IBD bursal lesions. Bursae were then harvested from each chicken and weighed. The results were calculated using the statistical methods in Example I. The nine day necropsy results are shown in Tables 10 and 11.

Referring to Tables 10 and 11, bursal lesions typical of IBD was found in seven percent (2/30) of the vaccinated birds and 100% of the positive controls. No incidence of bursal lesions were found in the negative controls.

The standard deviation computed from the negative control group was 1.12. Since the average ratio of the control group was 5.8, the normal range for this trial was 3.56 to 8.04 (normal range equals two standard deviations). The average ratio for the vaccinates (3.9) fell within this range while the average ratio for the positive control group (1.3) did not meet normal range.

EXAMPLE V

IBD-187EV—CROSS PROTECTION TRIAL

This trial was conducted to evaluate the protection levels obtained with IBD-BV3 and IBD-187EV vaccines against challenge with either the standard IBD USDA CV or IBD Variant E challenge virus.

Groups of 11 day old susceptible SCWL chickens were vaccinated via eye drop with either IBD-BV3 vaccine or IBD-187EV Master Seed Virus ($E_1$ $TC_{22}$ $E_1$ #061686). Each chicken received one dose of vaccine. Nonvaccinated chickens were held as controls.

Four weeks post-vaccination, challenges were conducted using either the USDA CV or Variant E challenge virus.

All chickens challenged with the USDA strain were evaluated for gross bursal lesions at four days post-challenge. Half of the chickens challenged with Variant E strain were examined at four days post-challenge for bursal lesions while the remainder were held for nine days. These birds were evaluated for bursal atrophy.

IBD-187EV vaccine induced adequate protection against standard USDA challenge virus. Both the four and nine day necropsy results indicated that adequate protection was obtained with IBD BV-3 vaccine against Variant E challenge.

This trial consisted of three groups of susceptible SCWL chickens, 11 days of age. For Group 1, 65 chickens were vaccinated with IBD-BV3 vaccine, serial #2406. For Group 2, 65 chickens were vaccinated with IBD-187EV Master Seed virus, $E_1$ $TC_{22}$ $E_1$ #061686. Group 3 consisted of 45 chickens held as unvaccinated controls.

For vaccination, one vial of each vaccine was rehydrated in 30 ml of eye dropper diluent. Each chicken was then vaccinated via eye drop route.

Four weeks post-vaccination, 20 chickens from each vaccine group and 10 controls were challenged with the standard IBD CV USDA lot #83-1. Forty chickens from each vaccine group and 20 controls were challenged with IBD Variant E CV E-1 #121685.

Four days post-challenge, all of the chickens challenged with the USDA CV and half of the chickens from each group challenged with the Variant E CV were necropsied for gross IBD bursal lesions. All chickens were held in Horsfal isolation cages prior to IBD challenge.

Nine days post-challenge, the remainder of the chickens challenged with the Variant E CV and the unchallenged negative controls were killed and individually weighed. Bursae were then harvested and weighed. The results were calculated using the statistical methods in Eample I. Four day necropsy results are shown in Table 12, 13 and 14.

TABLE 10

| | | NINE DAY NECROPSY RESULTS | | | |
|---|---|---|---|---|---|
| TREATMENT | ROUTE | VACCINE DOSE/BIRD | # BIRDS | POST-CHALLENGE # POS/TOTAL | LESIONS % PROT. |
| IBD-187EV Vac. $E_4$ #081886 (1:10 dil) | $H_2O$ | $10^{2.59}EID_{50}$ | 30 | 2/30 | 93 |
| Neg. Controls (Unchallenged) | — | — | 10 | 0/10 | —* |
| Pos. Controls | — | — | 10 | 10/10 | 0** |

*Protection was not measured as birds were unchallenged.
**Lesions include severe bursal atrophy.

TABLE 11

| SUMMARY OF BURSA/BODY WEIGHT RATIOS | | |
|---|---|---|
| TREATMENT GROUP | AVG. BURSA/BODY WEIGHT RATIO | STANDARD DEVIATION* |
| Vaccinates | 3.9 | — |
| Positive Controls | 1.3 | — |
| Negative Controls | 5.8 | 1.12 |

*Range for determining significancy of average ratios is two standard deviations or 2.24. Therefore, for purposes of this test, normal range is 3.56 to 8.04.

Referring to Tables 12, 13 and 14, the chickens vaccinated with IBD BV3 vaccine exhibited 100% protection against USDA challenge while the chickens vaccinated with IBD-187EV Master Seed showed 95% protection. In the control groups 100% of the chickens succumbed to challenge. In both Variant E and USDA vaccinated groups, incidence of bursal lesions were found in only 5% of the chickens while 100% of the controls succumbed to challenge.

Nine day necropsy results are shown in Tables 2 and 3. The average bursa/body weight ratios were 3.2 for the BV-3 group, 4.5 for the 187EV group, 1.4 for the positive control group, and 4.9 for the negative control group. The normal range as determined by calculation of a standard deviation of the negative control group was 2.3 to 7.5.

Obviously many modifications and variations of the present invention are possible in light of the above teachings. It is therefore to be understood that within the scope of the appended claims the invention may be practiced otherwise than as specifically described.

TABLE 12

4 DAY NECROPSY RESULTS

| TREATMENT | CHALLENGE | | | |
|---|---|---|---|---|
| | USDA | | VARIANT E | |
| | # POS/TOTAL | % PROTECTION | # POS/TOTAL | % PROTECTION |
| IBD BV-3 Vac. (Serial 2406) | 0/20* | 100 | 1/20 | 95 |
| IBD-187EV Master Seed ($E_1$ $TC_{22}$ $E_1$ #061686) | 1/20 | 95 | 1/20 | 95 |
| Positive Controls | 10/10 | 0 | 10/10 | 0 |

*Significant number of birds demonstrated bursal atrophy.

TABLE 14

SUMMARY OF BODY AND BURSAE WEIGHTS

| TREATMENT | AVERAGE BURSA/ BODY WEIGHT RATIO | STANDARD DEVIATION |
|---|---|---|
| IBD BV-3 Vac. (Serial 2406) | 3.2 | — |
| IBD-187EV Master Seed ($E_1$ $TC_{22}$ $E_1$ #061686) | 4.5 | — |
| Negative Controls | 4.9 | 1.3* |
| Positive Controls | 1.4 | — |

*Range for determining significance of ratios is two standard deviations or 2.6. Therefore, for purpose of this test, normal range is 2.3 to 7.5.

What is claimed is:

1. An attenuated Infectious Bursal Disease virus strain, VR2161.

2. A vaccine effective against Infectious Bursal Disease in poultry, comprising:
   an attenuated infectious bursal disease virus strain, VR2161; and
   an inert pharmaceutically acceptable carrier or diluent.

3. The vaccine of claim 2 administered in dosages from about log 2 to about log 5 $EID_{50}$.

4. The vaccine of claim 2 further containing one or more live or inactivated avian viruses.

5. The vaccine of claim 2 further containing one or more live or inactivated virus selected from the group consisting of New Castle Disease Virus, Infectious Bronchitis Virus, Reo Virus, and Adeno Virus.

6. The vaccine of claim 2 further containing one or more adjuvants.

7. The vaccine of claim 6 wherein said adjuvant is selected from the group consisting of aluminum hydroxide, aluminum phosphate, plant or animal oils.

8. The vaccine of claim 2 further containing one or more stabilizers.

9. The vaccine of claim 8 wherein said stabilizer is selected from the group consisting of carbohydrates such as sorbitol, manitol, starch, sucrose, dextrin, or glucose, proteins such as albumin or casein, and buffers such as alkaline metal phosphate.

10. A method for controlling Infectious Bursal Disease in poultry, comprising:
    administering a vaccine prepared from an attenuated infectious bursal disease virus strain, VR2161.

11. The method of claim 10 wherein the attenuated infectious bursal disease virus strain is inactivated.

12. The method of claim 10 wherein the vaccine is administered nasally, ophthalmically, by injection, in drinking water, or by exposure.

13. The method of claim 10 wherein the vaccine is administered using mass administration methods.

14. The method of claim 13 wherein the vaccine is administered in drinking water or by spraying the animals environment.

15. The method of claim 10 wherein the vaccine is administered by injection.

16. The method of claim 15 wherein the vaccine is administered parenterally.

17. A vaccine effective against Infectious Bursal Disease in poultry, comprising:
    an inactivated infectious bursal disease virus strain, VR2161; and
    an inert pharmaceutically acceptable carrier or diluent.

18. The vaccine of claim 17 administered in dosages from about log 5 to about log 8 $EID_{50}$.

19. The vaccine of claim 17 further containing one or more live or inactivated avian viruses.

20. The vaccine of claim 19 further containing one or more live or inactivated virus selected from the group consisting of New Castle Disease Virus, Infectious Bronchitis Virus, Reo Virus, and Adeno Virus.

21. The vaccine of claim 17 further containing one or more adjuvants.

22. The vaccine of claim 21 wherein said adjuvant is selected from the group consisting of aluminum hydroxide, aluminum phosphate, plant or animal oils.

23. The vaccine of claim 17 further containing one or more stabilizers.

24. The vaccine of claim 23 wherein said stabilizer is selected from the group consisting of carbohydrates such as sorbitol, manitol, starch, sucrose, dextrin, or glucose, proteins such as albumin or casein, and buffers such as alkaline metal phosphate.

* * * * *

UNITED STATES PATENT AND TRADEMARK OFFICE
CERTIFICATE OF CORRECTION

PATENT NO. : 4,824,668
DATED : April 25, 1989
INVENTOR(S) : Fred W. Melchior, Jr. and Lillian Melson It is certified that error appears in the above-identified patent and that said Letters Patent is hereby corrected as shown below:

Column 1, line 9, after the word "disease" insert --virus--
Column 3, line 35, "abou" should read --about--
Column 9, line 61, "challenged" should read --challenge--
Column 11, line 46, "tetrations" should read --titrations--
Column 11, line 55, "$TC_{22}$ #061686" should read --$TC_{22}\ E_1$ #061686--

Signed and Sealed this

Third Day of July, 1990

Attest:

HARRY F. MANBECK, JR.

Attesting Officer

Commissioner of Patents and Trademarks